United States Patent [19]

Cuscurida et al.

[11] 4,222,954
[45] Sep. 16, 1980

[54] IODOPHORE COMPOUNDS

[75] Inventors: Michael Cuscurida; George P. Speranza, both of Austin, Tex.

[73] Assignee: Texaco Development Corp., White Plains, N.Y.

[21] Appl. No.: 957,257

[22] Filed: Nov. 2, 1978

Related U.S. Application Data

[63] Continuation-in-part of Ser. No. 873,025, Jan. 27, 1978, abandoned.

[51] Int. Cl.$^2$ .................. C07C 69/00; C10M 3/24; A61K 33/18; A61K 31/265
[52] U.S. Cl. ...................... 260/463; 252/54; 252/106; 424/150; 424/301
[58] Field of Search .............. 260/463; 528/370, 112

[56] References Cited

U.S. PATENT DOCUMENTS

| | | | |
|---|---|---|---|
| 3,248,415 | 4/1966 | Stevens | 260/463 |
| 3,332,980 | 7/1967 | Leary et al. | 260/463 |
| 3,721,693 | 3/1973 | Fein et al. | 260/463 |
| 3,911,107 | 10/1975 | Krezanoski | 424/150 |
| 4,022,814 | 5/1977 | Newton | 260/463 |
| 4,072,704 | 2/1978 | Langdon | 260/463 |

*Primary Examiner*—Donald G. Daus
*Assistant Examiner*—M. C. Eakin
*Attorney, Agent, or Firm*—Carl G. Ries; Robert A. Kulason; James L. Bailey

[57] ABSTRACT

Covers iodophore compounds prepared by reacting a polyether polycarbonate and and an iodine-supplying compound, preferably iodine itself.

4 Claims, No Drawings

IODOPHORE COMPOUNDS

REFERENCE TO RELATED APPLICATIONS

This application is a continuation-in-part application of copending application Ser. No. 873,025, filed Jan. 27, 1978, now abandoned.

BACKGROUND OF THE INVENTION

1. Field of the Invention

This invention relates to iodo compounds particular useful as bactericides.

2. Description of the Prior Art

Compounds containing iodo groups which are useful as bactericides are well known in the art. See for example, U.S. Pat. Nos. 3,984,341; 3,285,816; and 3,326,806; and British Pat. No. 1,666,437.

However such iodo compounds in many instances have a number of deficiencies either from an activity standpoint or from a standpoint of consideration of their chemical and physical properties. Thus, for example, many such iodo compounds, particular when used in an aqueous medium cause foaming problems, and in some cases even though sufficiently active their use could be hindered due to this distinct drawback.

Therefore it becomes an object of the invention to provide a new class of iodophores which particularly are characterized by their low foaming properties.

SUMMARY OF THE INVENTION

In its broadest aspect the present invention comprises a new class of iodophore compounds prepared by reacting certain polyether polycarbonate and an iodine-supplying compound. Said polyether polycarbonate is a compound prepared by reacting a monohydroxy organic compound of the type shown below acting as an initiator with alkylene oxide and carbon dioxide, followed by reaction of the thus formed polyether polycarbonate with iodine itself.

DESCRIPTION OF THE PREFERRED EMBODIMENTS

In more detail, the practice of the present invention relates to iodophore compounds prepared by reacting a polyether polycarbonate and iodine wherein the polyether polycarbonate is prepared by first providing an organic monohydroxy compound acting as an initiator with alkylene oxide and carbon oxide. As will be seen later, the organic hydroxy initiator contains a plurality of ether groups along with the hydroxy group present. It is greatly preferred that the hydroxy initiator be reacted with alkylene oxide and carbon dioxide in a simultaneous manner to form the polyether polycarbonate.

The low-foaming hydroxy reactants here essentially are of two classes. The first class includes compounds falling within the following formula:

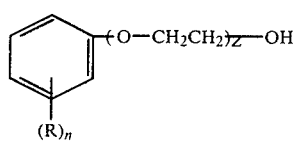

where R is a $C_1$–$C_{22}$ alkyl group, n is a integer of 1-3, and z is a number ranging from 2 to 20. Z more preferably is 2-15 and most preferably is 3-10. R most preferably is $C_8$–$C_{12}$.

The other class of organic hydroxy initiator compounds are those where in the above formula:

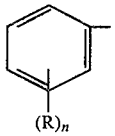

is replaced by $R_1$ where $R_1$ is a $C_6$–$C_{22}$ straight or branched chain alkyl or alkenyl group.

The polyether polycarbonate employed to react with the iodine compound of iodine-releasing compound may be prepared via a wide variety of techniques as known in the art. One particularly preferred technique is to provide one or more of the just mentioned hydroxy initiator compounds and react said compound with a lower alkylene oxide and carbon dioxide in a simultaneous manner. The lower alkylene oxide reactant is usually one containing 1-4 carbon atoms, and most preferably is either ethylene oxide, propylene oxide, or a mixed ethylene oxide/propylene oxide. The amount of alkylene oxide and carbon dioxide used most preferably ranges from 8:1 to 1:1 alkylene oxide to carbon dioxide in terms of a molar ratio. The molar ratio of alkylene oxide plus carbon dioxide to initiator again may be varied over a wide range. Usually such mole ratio ranges from 5:1 to 30:1.

The reaction of carbon dioxide and alkylene oxide with hydroxy initiator is adaptable to both batch and continuous processes in order to produce the water soluble polycarbonates useful in preparing the iodophore compounds.

The following examples illustrate typical iodophore compounds of the invention and their mode of preparation. It is understood, of course, that these examples are merely illustrative, and that the invention is not to be limited thereto.

EXAMPLE 1

This example will illustrate the preparation of a polyether polycarbonate useful in this invention.

748 g of the 12 mole ethylene oxide adduct of nonyl phenol and 4.5 g potassium stannate were charged into a one-gallon stirred autoclave. Ethylene oxide (845 g) and carbon dioxide (211 g) were then pressured into the autoclave and heated at 175° C. for six hours. The pressure reached a maximum of 1300 psig and equilibrated at 65 psig. The product was then neutralized with 18 g of a synthetic magnesium silicate, stripped, and filtered. The finished product (1482 g) was a light yellow, water-soluble, viscous liquid with the following properties:

| | |
|---|---|
| Hydroxyl No., mg KOH/g | 53.2 |
| Water, wt. % | 0.02 |
| Viscosity, °F., cs | |
| 100 | 967 |
| 210 | 63.8 |
| Surface tension (dynes; cm) | |
| 1% | 38.2 |
| 0.1% | 38.1 |
| 0.01% | 38.1 |

EXAMPLE 2

This example will illustrate the preparation of a polycarbonate polyether from the three mol ethylene oxide adduct of a $C_{12}$–$C_{13}$ alcohol.

Into a three-gallon stirred autoclave were charged 800 g of the alcohol, and 10.3 g. potassium stannate. Ethylene oxide (2640 g.) and carbon dioxide (660 g.) were then pressured into the reactor. The reaction mixture was then heated at 175°–202° C. for 4.75 hours. The pressure reached a maximum of 1525 psig and equilibrated at 95 psig. The product was then neutralized with 41.2 g. synthetic magnesium silicate, vacuum stripped to remove volatiles and filtered. The finished product (3459 g.) had the following properties:

| | |
|---|---|
| Acid No., mg KOH/g | 0.056 |
| Hydroxyl No. mg KOH/g | 55.9 |
| Water, wt. % | 0.046 |
| pH in 10:6 isopropanol-water | 7.4 |
| Viscosity, °F., cs | |
| 100 | 567 |
| 210 | 46 |
| Saponification No., mg KOH/g | 203.8 |
| Carbon dioxide content, wt. % | 16 |
| Surface tension (dynes/cm) | |
| 1% | 29.5 |
| 0.1% | 30.6 |
| 0.01% | 33.2 |

EXAMPLE 3

This example will illustrate the preparation of an iodophore by reaction of iodine with the polyether polycarbonate of Example 1.

Into a 500 ml three-necked flask equipped with a stirrer, thermometer, condenser, and nitrogen purge was charged 225 grams of the polycarbonate polyether prepared by reaction of the 12 mole ethylene oxide adduct of nonyl phenol with ethylene oxide and carbon dioxide. Maintaining a nitrogen purge, the polycarbonate polyether was heated to 68° C. and 75 g. iodine crystals added over a 20 minute period. The reaction mixture was then heated at 68°–78° C. for two hours. The resultant product was a viscous, homogenous liquid with dark iodine color. After 8 months storage in glass the product was filtered through a glass filter and titrated for available iodine using a sodium thiosulfate titration.

| Analysis | Percent |
|---|---|
| Total iodine | 25 |
| Available iodine | 16.2 |
| Available/total, % | 64.8 |

EXAMPLE 4

Using the general procedure of Example 3 an iodophore was prepared by reaction of 75 g. iodine with 225 g. of the polyether polycarbonate of Example 2. The product had the following properties after standing overnight.

| Analysis | Percent |
|---|---|
| Total iodine | 25 |
| Available iodine | 19.6 |
| Available/total, % | 78.4 |

In order to provide iodophore compounds possessing both microbiocidal activity concomitant with low foaming properties it is necessary that they have a structure as depicted above. Seemingly similar iodophore compounds, particularly varying as to the base initiator only as to an apparent small difference have been found here not to be low foamers and are therefore deficient for use in many area as, for example, in dish washing formulations, and as antiseptics and sterilants for various end-uses.

EXAMPLE 5

This example will illustrate that foam heights as determined by the Ross Miles test are significantly lower for the iodophores based on the polycarbonate polyether of this invention as compared to those based on prior art carriers such as the 12 mole ethylene oxide adduct of nonyl phenyl.

| Polycarbonate polyether compound | Ross Miles (0.1% Initial | Foam Height 120° F.) Five Min. |
|---|---|---|
| Example 1 | 42 | 18 |
| Example 2 | 50 | 25 |
| 12 mole ethylene oxide adduct of nonyl phenol | 107 | 55 |

The compounds here are useful as microbiocidal agents. The term "microbiocidal agent" is meant to designate a chemical substance which has killing and/or inhibiting action on such microorganisms as, for example, bacteria, fungi, algae, protozoa and the like.

Thus, for example, the compounds here may be useful in inhibiting and controlling the growth and reproduction of microorganisms in aqueous recirculating waters and industrial processes. As an example, the iodophore compounds may be used as biological control agents in paper mill water systems in order to prevent the build up of microbiological slime due to the accumulation of microorganisms. Likewise, the microbiocides here may be used to treat industrial cooling systems. In like manner they may be effectively employed in reducing and/or inhibiting growth of microorganisms in air conditioning equipment, internal combustion engines, in the secondary recovery of petroleum in the process known as water-flooding, in water wells, and similarly related industrial fluid systems.

The microbiocides may also be used to control harmful organisms in environmental conditions other than that of water. Thus, the iodophores here may be used as antiseptics, disinfectants, fumigants, fungistats, fungicides, preservatives, chemical and physical sterilants, and pasteurization agents. The compounds may also have use as insecticides.

The microbiocides may specifically be used to treat hydrocarbon fluids containing minor amounts of aqueous liquids. While pure hydrocarbon fluids in most instances are not appreciably susceptible to bacterial or fungal attack those fluids containing even as little as 10 ppm of water are prone to attack, since the aqueous phase becomes an excellent environmental medium for the microbes. Thus, the microbiocides of the invention may be added to fuel oils, jet fuels and gasoline to prevent sludge formation in the hydrocarbon fluid and production of corrosive acids. More specifically, the compounds here may be added to large storage tanks, to storage drums, to the run-down line leading from the last operation of refining a petroleum fluid or to any storage or transfer area which contains a finished petroleum product. Thus, protection, particularly against bacteria and fungi is afforded by addition of the iodophore compounds here to a hydrocarbon product.

Lastly, the compounds set out here may be used to prevent inhibition of chemical deterioration or spoilage of organic substances due to static microbic attack. Thus, the iodophore compounds of the invention may be used as preservatives to protect carbohydrates, proteins and synthetic organic materials against such microbic attack. Various additives useful in the paper industry and other related industries which may be stabilized from chemical degradative microorganism attack by means of addition of the compounds here are starch, dextrin, glucose, casein, soya protein, animal and fish glues, sodium carboxymethyl cellulose, polyvinylchloride-butadiene copolymers, polyvinyl acetate latexes, acrylates, and others.

As shown above, the iodophore compounds of the invention are particularly useful in treating aqueous solutions against microbic attack by virtue of their low foaming property.

We claim:

1. An iodophore compound prepared by reaction of iodine with a polyether polycarbonate formed by reaction of a lower alkylene oxide, carbon dioxide and an organic hydroxy initiator compound falling within the following structural formula:

where $R_1$ is a $C_{6-22}$ straight or branched chain alkyl or alkenyl group or represents

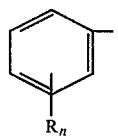

where R is a $C_1$–$C_{22}$ alkyl group, n is an integer of 1–3, and z is an integer of 2–20 wherein the ratio of alkylene oxide plus carbon dioxide to initiator ranges from 1:1 to 30:1, and the ratio of alkylene oxide to carbon dioxide ranges from 8:1 to 1:1.

2. The compound of claim 1 wherein said alkylene oxide is ethylene oxide, propylene oxide or mixed ethylene oxide/propylene oxide.

3. The compound of claim 1 wherein said organic hydroxy compound is an ethylene oxide adduct of nonyl phenol.

4. The compound of claim 1 wherein said initiator is an ethylene oxide adduct of a $C_{12}$–$C_{13}$ alcohol.

* * * * *